United States Patent
Caillouette

[19]

[11] Patent Number: 6,013,036
[45] Date of Patent: Jan. 11, 2000

[54] VAGINAL MULTIPLE CONDITION DETECTION APPARATUS AND METHOD

[76] Inventor: James C. Caillouette, 685 Oak Knoll Cir., Pasadena, Calif. 91106

[21] Appl. No.: 09/072,257

[22] Filed: May 4, 1998

Related U.S. Application Data

[63] Continuation-in-part of application No. 08/890,748, Jul. 11, 1997, Pat. No. 5,916,176, which is a continuation-in-part of application No. 08/699,251, Aug. 19, 1996, Pat. No. 5,735,801, which is a continuation-in-part of application No. 08/570,534, Dec. 11, 1995, Pat. No. 5,762,614, which is a continuation-in-part of application No. 08/537,379, Oct. 27, 1995, Pat. No. 5,577,512, which is a continuation-in-part of application No. 08/376,830, Jan. 23, 1995, Pat. No. 5,664,579, which is a continuation-in-part of application No. 08/295,399, Aug. 25, 1994, Pat. No. 5,425,377.

[51] Int. Cl.$^7$ ........................................... A61B 5/00
[52] U.S. Cl. ............................................... 600/572
[58] Field of Search ........................... 600/562, 569–572, 600/573, 584; 604/1; 33/511, 512, 755, 758–760

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,037,496 | 6/1962 | Melges . |
| 3,117,569 | 1/1964 | Wegner . |
| 3,319,621 | 5/1967 | Schwerin . |
| 3,507,269 | 4/1970 | Berry . |
| 3,509,872 | 5/1970 | Truhan . |
| 3,792,699 | 2/1974 | Robin et al. . |
| 4,820,259 | 4/1989 | Stevens .......................... 604/2 |
| 4,862,899 | 9/1989 | Bucaro ........................... 128/749 |
| 5,063,930 | 11/1991 | Nucci ............................ 128/632 |
| 5,147,288 | 9/1992 | Schiavo . |
| 5,253,652 | 10/1993 | Fast ............................. 128/756 |

OTHER PUBLICATIONS

"Vulvovaginitis", vol. 1, Chapter 37, Ronald M. Meltzer.
"Urinary Incontinence and Related Urogenital Symptoms in Elderly Women", Ulla Molander, Scandinavian Association of Obstetricians and Gynecologists, Supplement 158, vol. 72, 1993.
"Estrogen Deprivation and Vaginal Function in Postmenopausal Women", James P. Semmens, MD, Gorm Wagner, MD.
Peter Smith, Dept. of Obstetrics & Gynecology, University Hospital, S–751 85 Uppsala, Sweden "Estrogens and the Urogenital Tract", 1993.
Gloria Bachmann, Maturitas 22 Suppl. (1995) S21–S29 "The Estradiol Vaginal Ring—A Study of Existing Clinical Data".

*Primary Examiner*—Max Hindenburg
*Attorney, Agent, or Firm*—William W. Haefliger

[57] ABSTRACT

In apparatus for detecting first and second conditions in the vagina or urethra, the combination comprising an elongated carrier insertible endwise into the vagina; first structure at a first location on the carrier for use in detecting the first condition, and second structure at a second location on the carrier for use in detecting the second condition, portions of first and second structures being inserted into the vagina or urethra, by manipulation of the carrier, and to be subsequently withdrawn, for use in detecting conditions.

44 Claims, 11 Drawing Sheets

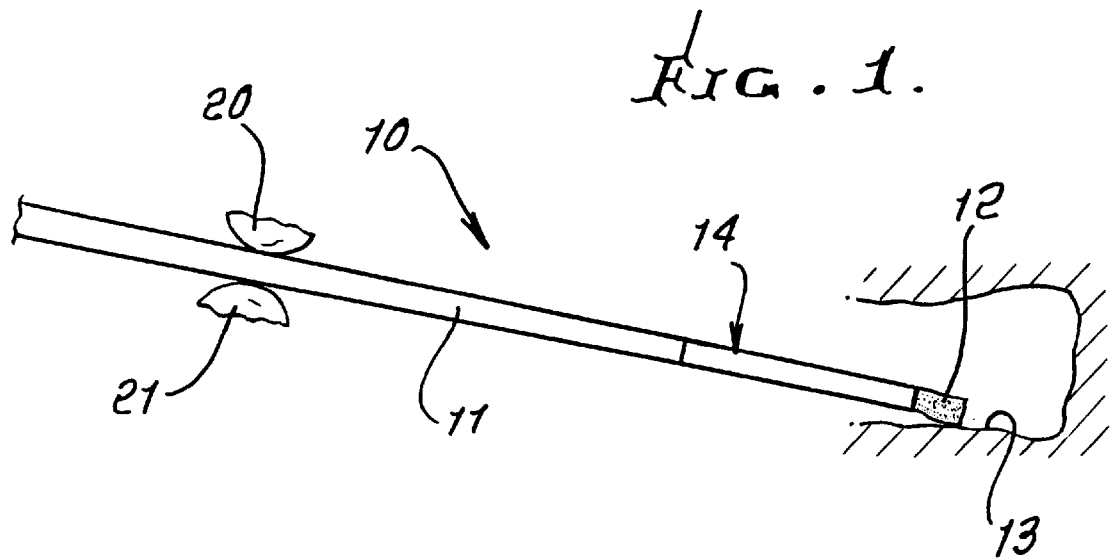
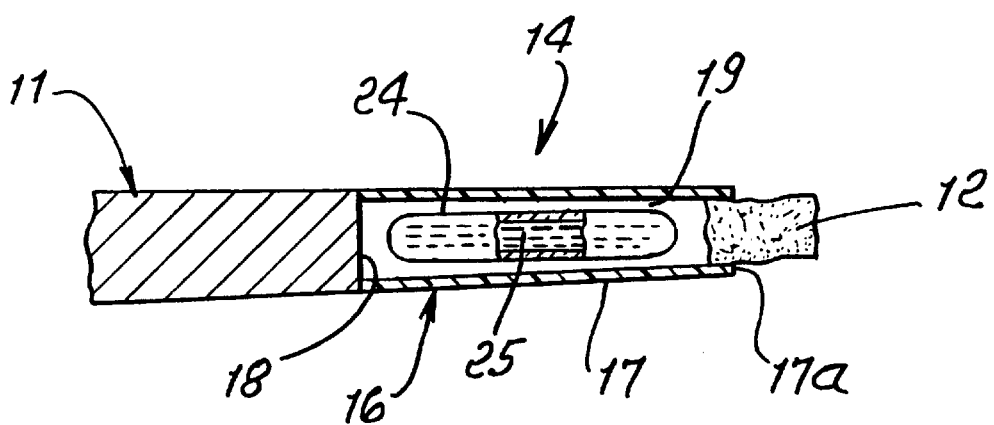

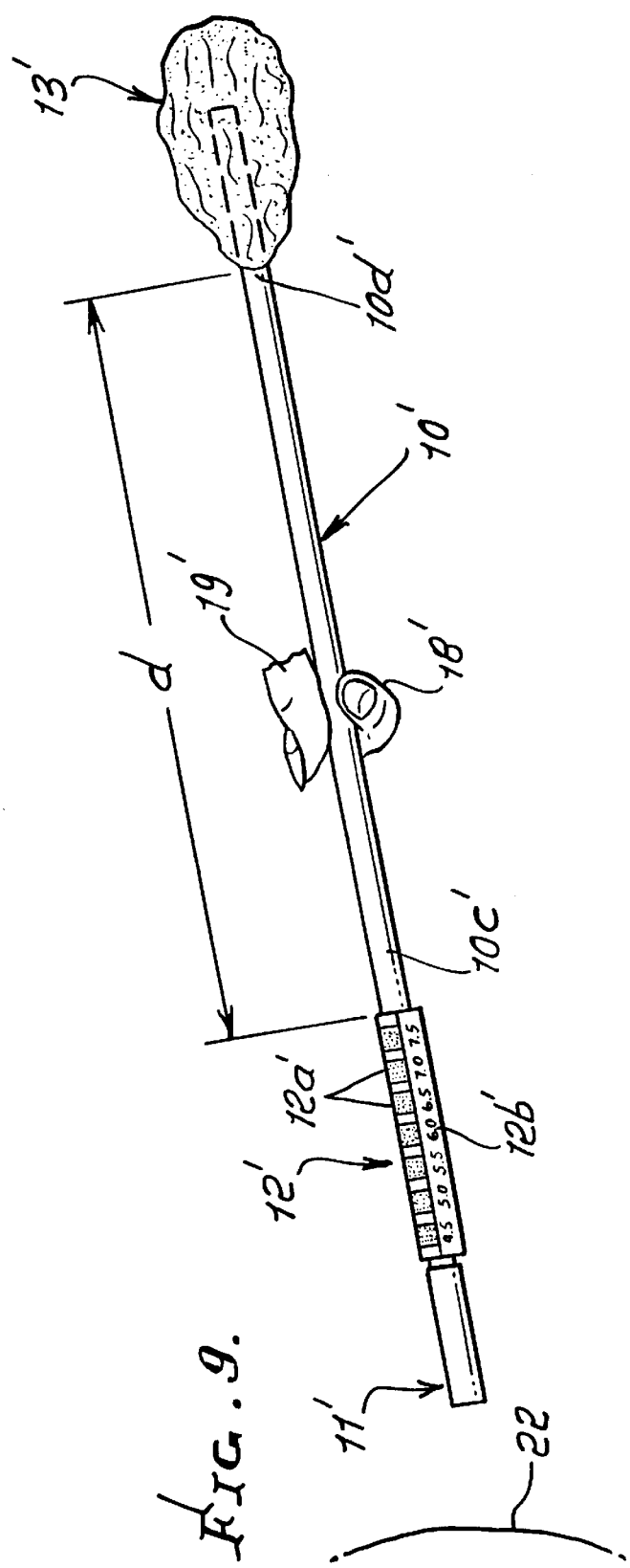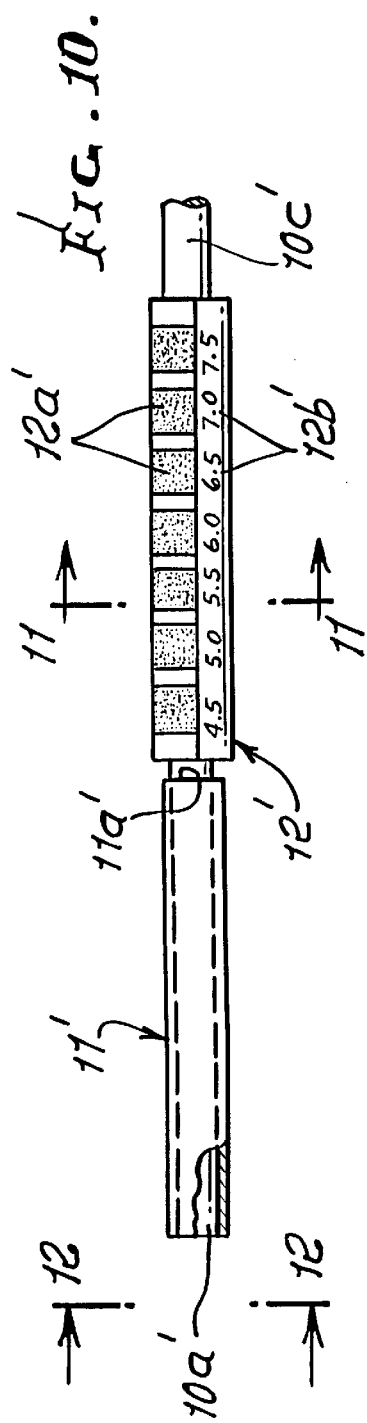

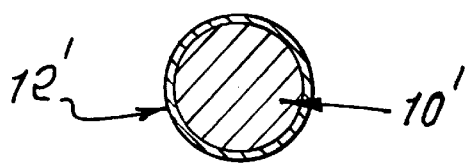
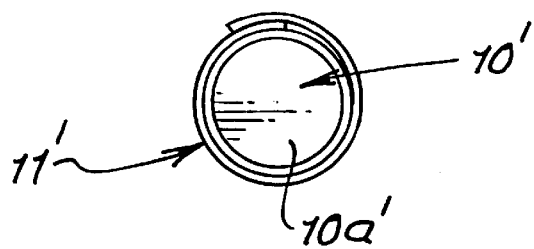
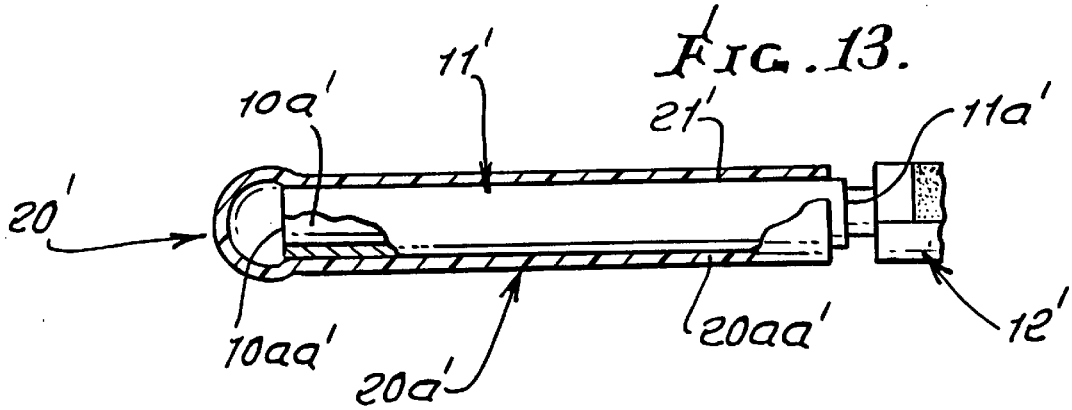
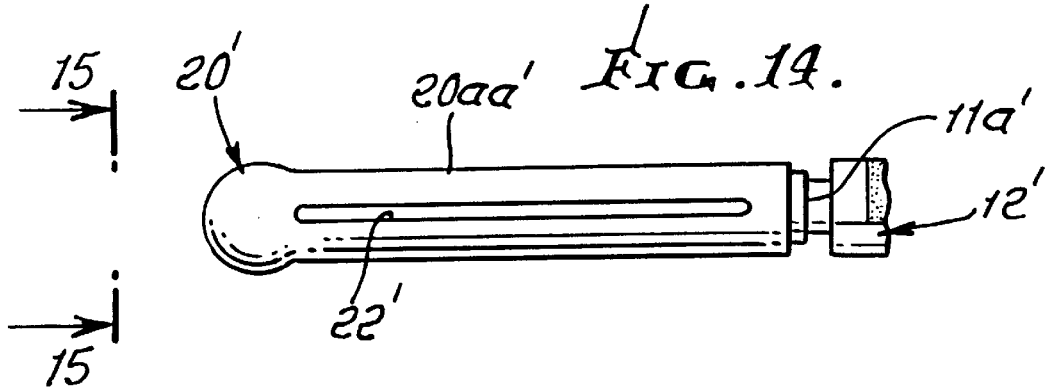

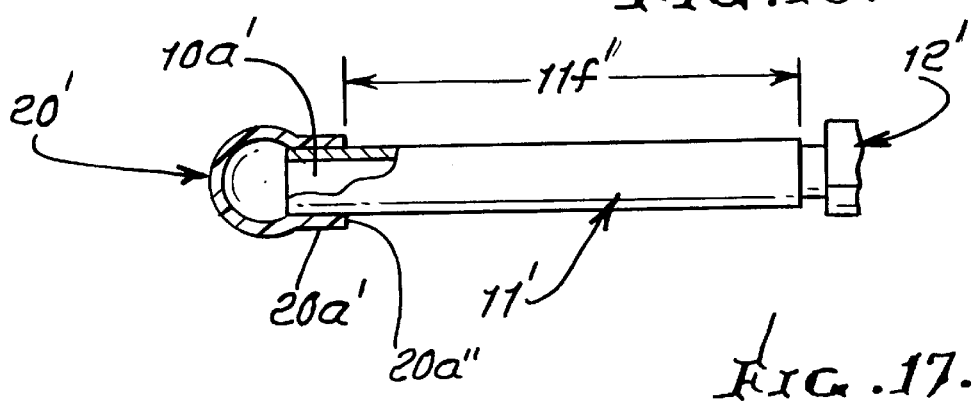
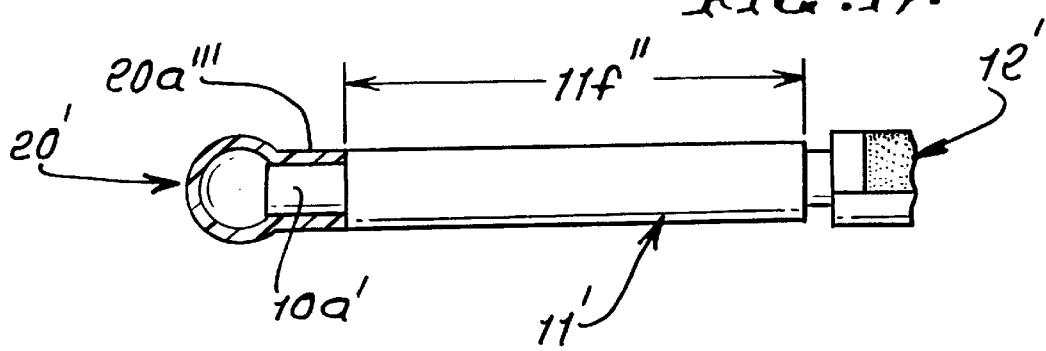
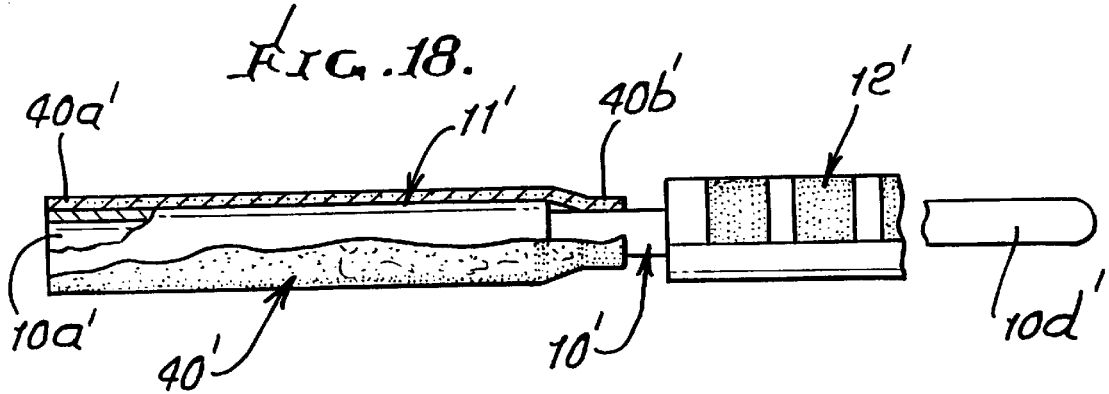
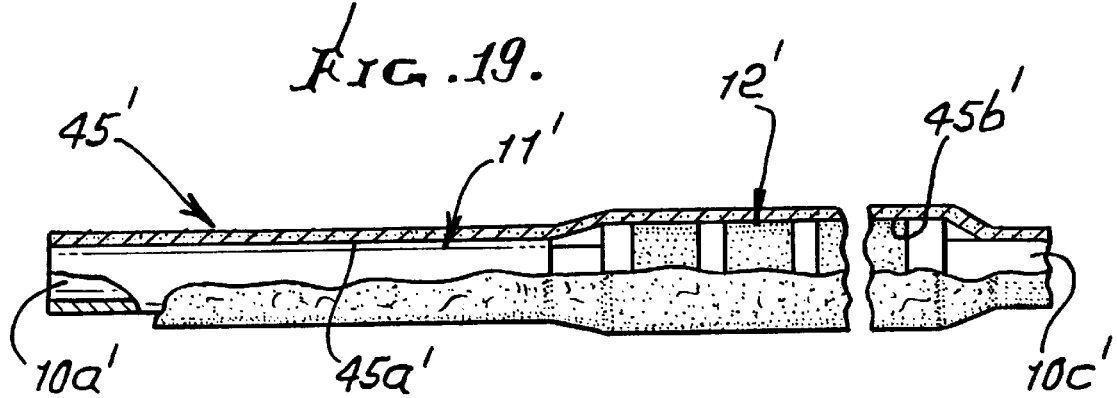

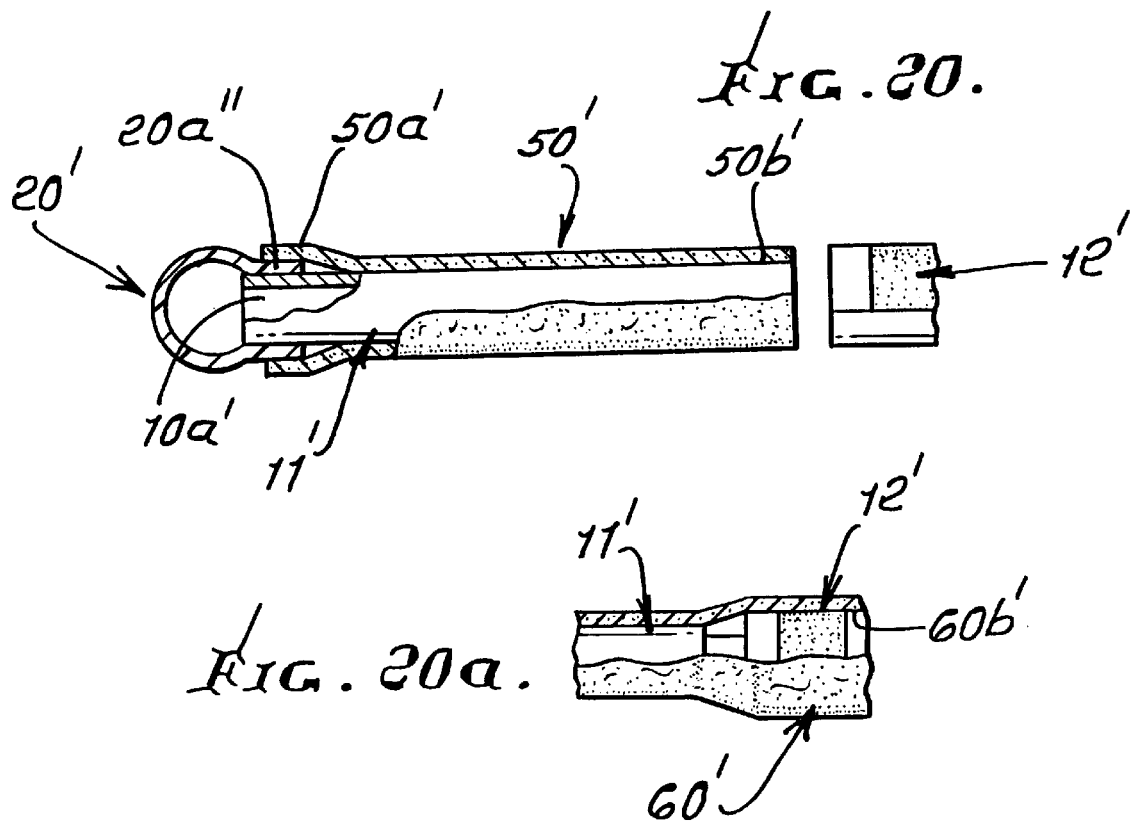
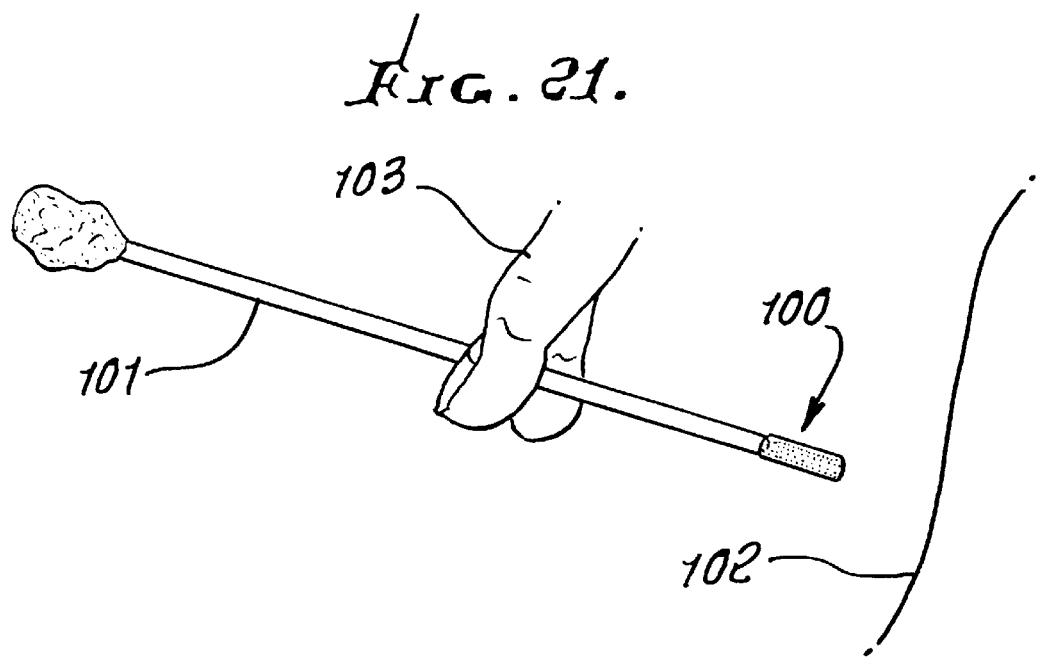

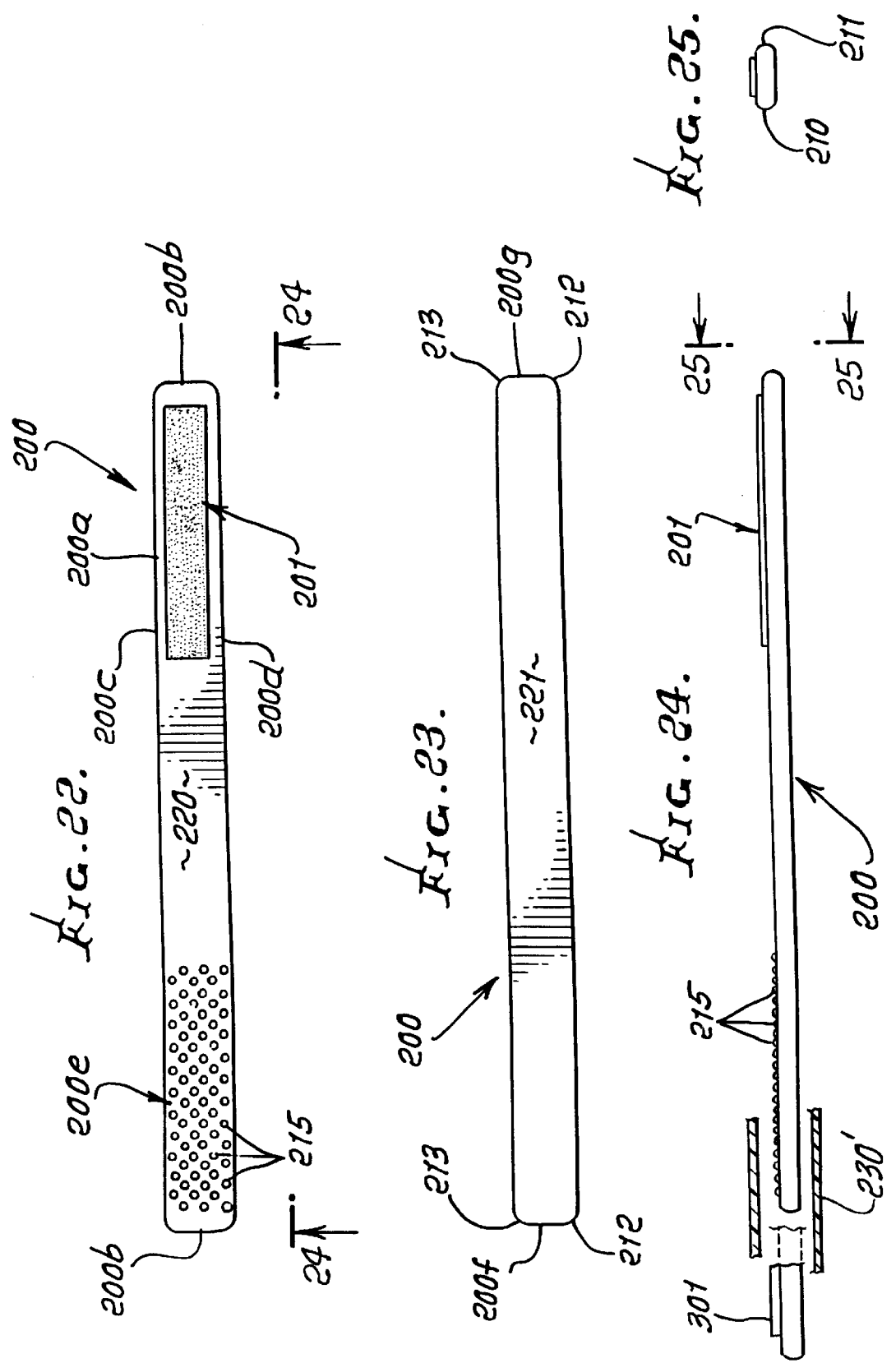

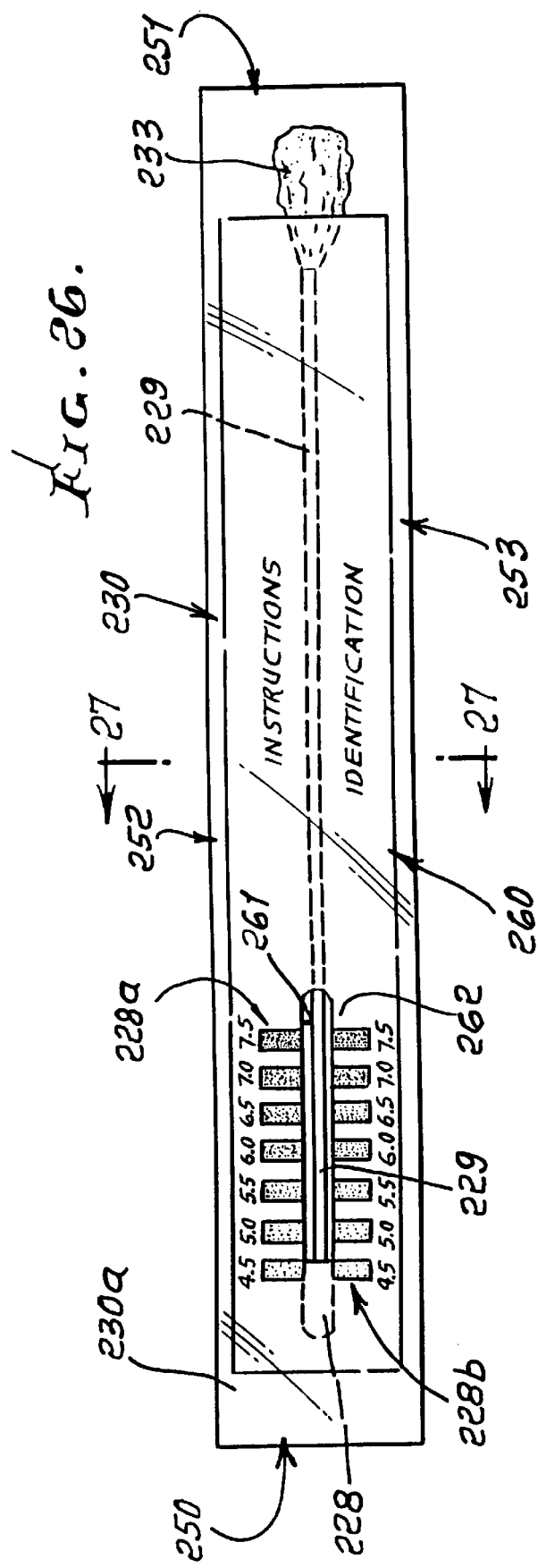
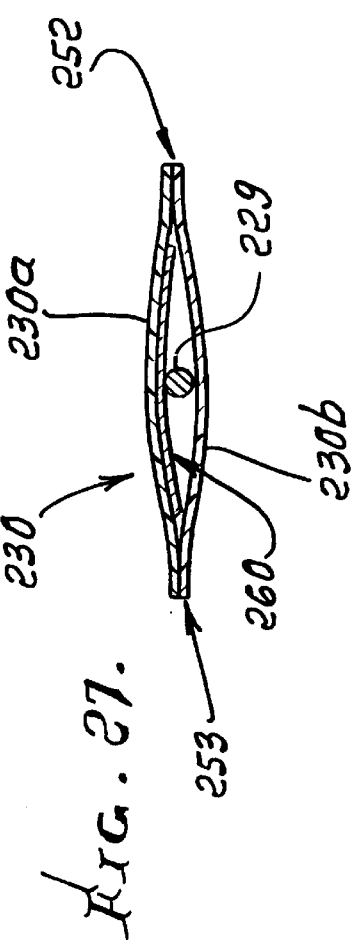
FIG. 26.
FIG. 27.

VAGINAL MULTIPLE CONDITION DETECTION APPARATUS AND METHOD

This application is a continuation-in-part of prior U.S. application Ser. No. 08/890,748 filed Jul. 11, 1997, now U.S. Pat. No. 5,916,176 which is a continuation-in-part of prior U.S. application Ser. No. 08/699,251 filed Aug. 19, 1996, now U.S. Pat. No. 5,735,801, which is a continuation-in-part of prior U.S. application Ser. No. 08/570,534 filed Dec. 11, 1995, now U.S. Pat. No. 5,762,614 which is a continuation-in-part of prior U.S. application Ser. No. 08/537,379 filed Oct. 27, 1995, now U.S. Pat. No. 5,577,512, which is a continuation-in-part of prior U.S. application Ser. No. 08/376,830 filed Jan. 23, 1995, now U.S. Pat. No. 5,664,579, which is a continuation-in-part of prior U.S. application Ser. No. 08/295,399 filed Aug. 25, 1994, now U.S. Pat. No. 5,425,377.

BACKGROUND OF THE INVENTION

This invention relates generally to detection of different conditions in the vagina, examples being pH of vaginal moisture, and the presence of pathogenic bacterial in such moisture.

There is need for apparatus and method to quickly and easily detect or determine such multiple conditions, as during an examination. In this regard, there is also need to employ such pH detection in estrogen replacement therapy, or changes in dosage of estrogen or estradiol.

SUMMARY OF THE INVENTION

It is a major object of the invention to provide method and apparatus meeting the above need. Basically, apparatus of the invention is adapted for detection of first and second conditions in the vagina, such apparatus including:

a) an elongated carrier insertible endwise into the vagina, b) first structure at a first location on the carrier for use in detecting said first condition, c) and second structure at a second location on the carrier for use in detecting said second condition, d) portions of first and second structures being inserted into the vagina or urethra, by manipulation of the carrier, and to be subsequently withdrawn, for use in detecting said conditions.

As will appear, the first structure may take the form of a pH detector or detection means; and the second structure may take the form of a pathogenic bacteria detector means. The latter may include i) a flexible outer container supported on the carrier, ii) a vaginal moisture absorbing swab at one end of the carrier to communicate with the interior of the outer container, iii) a frangible inner container protectively located within the outer container, and a flowable aqueous alkaline fluid reactant within the inner container, iv) whereby pressure exerted on the outer container sufficient to rupture the inner container thereby releases reactant into the interior of the outer container to enable reactant fluid flow to the swab, for reaction with bacteria containing vaginal moisture absorbed into the swab, v) and whereby a gaseous product of said reaction may be detected, by characteristic odor.

Another object is to provide a third structure on the carrier to provide release of a secondary odor corresponding to a primary odor created during such use of said second structure, for whiff comparison. The third structure may comprise a cover releasably adherent to the carrier, and a secondary odor source on the carrier concealed by that cover.

The pH detector structure concerns the discovery that the acidity (pH) or pH(acidity) level of a moist wall surface of the vagina or urethra can be employed in estrogen or estradiol need determination. The method of using that pH detection structure for determining need for estrogen or estradiol increase or decrease includes the steps:

a) determining local acidity proximate a moist wall surface of the vagina, or urethra, as differing from desired threshold level, and in the substantial absence of bacterial vaginosis, or other contaminants such as medications, blood, semen, b) and administering sufficient estrogen or estradiol to result in change in acidity toward such level or a pH of about 4.5 without menopausal signs or symptoms.

Typically, administering of sufficient estrogen or estradiol may be effected on a periodic regular basis, as for example increased or decreased dosage (for example orally) on a daily basis, and in increasing amounts, and said determination of local acidity is repeated, whereby such local acidity is ultimately determined to have reached desired level. Estrogen may be given orally, by injection, by skin patch, by vaginal insertion, by subdermal pellet, by vaginal ring, or by applying cream to a dermal surface.

Yet another object is the carrying out of such determination of local acidity as by employing an acidity indicator, for contacting the wall surface of the vagina or urethra. Such an indicator may desirably include one of the following:

i) NITRAZINE© paper ii) phenaphthazine on a carrier iii) a material or materials exhibiting different colorations or other indicators as a function of pH level.

A strip of material may be used to carry the indicator, and such a strip may be employed in contacting the vaginal or urethral wall. One method of use is to provide the strip of material on the applicator, an example being the carrier stick, which is easily manipulable.

A further object is to provide a pH level indicator comprising a material or materials exhibiting colorations corresponding to pH levels of moisture of the wall surface of the vagina, or urethra, such colorations being different for different pH levels. The desired threshold level of acidity is approximately 4.2–4.5.

Yet another object is to provide a method that includes the steps:

a) providing an acidity sensing means on a carrier, b) providing a protective porous layer adjacent said sensing means, c) manipulating the carrier proximate vaginal moisture, and including allowing vaginal and/or urethral moisture to penetrate said porous layer for contact with said sensing means, d) and detecting a vaginal and/or urethral moisture produced change in said sensing means for determining need for beginning estrogen replacement therapy or a change in estrogen or estradiol dose to be administered to a human female.

An additional object is to measure vaginal or urethral pH for screening purposes, a vaginal or urethral pH level of 4.5 being consistent with a physiologic serum estradiol and the absence of bacterial vaginosis. An elevated vaginal pH in the 5.0–6.5 range suggests a diagnosis of either bacterial vaginosis or decreased serum estradiol. In patients with an elevated pH, vaginal culture or other biological testing should establish the diagnosis. In the absence of vaginosis, a vaginal pH of 6.5–7.5 is strongly suggestive of a low serum estradiol or menopause. Titration of estradiol level by vaginal or urethral pH during estrogen replacement therapy is then carried out.

Yet another object is to provide a) a support package, b) color comparison measurement elements carried by the package to allow their comparison with said pH detector after exposure of the detector to moisture the pH of which is to be determined.

All three of the structures on the carrier, together with the carrier in the form of a stick, may be receivable in the support package.

These and other objects and advantages of the invention, as well as the details of an illustrative embodiment, will be more fully understood from the following specification and drawings, in which:

DRAWING DESCRIPTION

FIG. 1 is a view showing use of an elongated assembly incorporating the invention;

FIG. 2 is an enlarged section taken lengthwise through an end portion of the FIG. 1 assembly;

FIG. 9 is a side elevational view of stick apparatus incorporating the invention;

FIG. 10 is an enlarged side view of one end portion of the FIG. 9 stick apparatus;

FIG. 11 is an enlarged section taken on lines 11—11 of FIG. 10;

FIG. 12 is an enlarged end view taken on lines 12—12 of FIG. 10;

FIG. 13 is an elevation, partly in section, showing a modification;

FIG. 14 is a side elevation of the FIG. 13 modification;

FIG. 15 is an end view taken on lines 15—15 of FIG. 14;

FIG. 16 is an elevation showing a further modification;

FIG. 17 is an elevation showing yet another modification;

FIG. 18 is a view like FIG. 10 showing a protective porous layer applied over a pH indicator strip;

FIG. 19 is a view like FIG. 18, but showing the protective layer also applied over the color comparison measurement means;

FIG. 20 is a view like FIG. 16, showing a protective porous layer applied over a pH indication strip;

FIG. 20a is a view like FIG. 20, but showing the protective porous layer extending over the color comparison measurement means;

FIG. 21 is a perspective view showing pH indictor manipulation manually;

FIG. 22 is a plan view of the top side of a modified stick apparatus;

FIG. 23 is a plan view of the bottom side of the FIG. 22 stick apparatus;

FIG. 24 is an edge view taken on lines 24—24 of FIG. 22;

FIG. 25 is an end view taken on lines 25—25 of FIG. 24;

FIG. 26 is a plan view of modified apparatus;

FIG. 27 is an enlarged section taken on lines 27—27 of FIG. 26;

Figure 28:
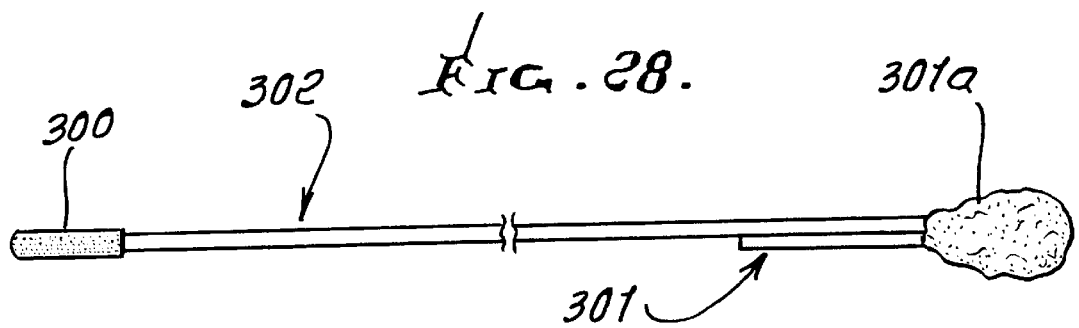
Figure 29:
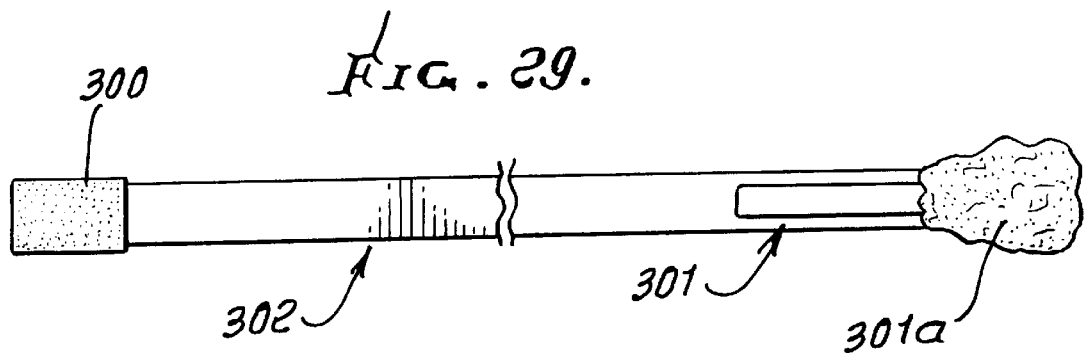
Figure 30:
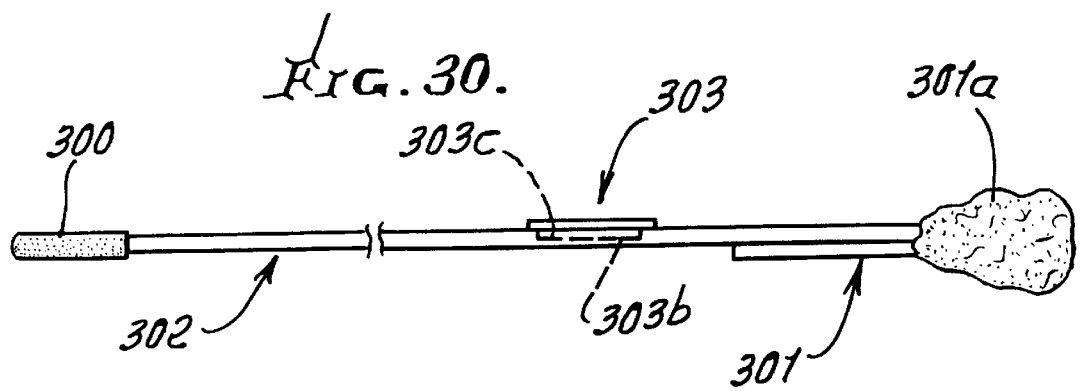
Figure 31:
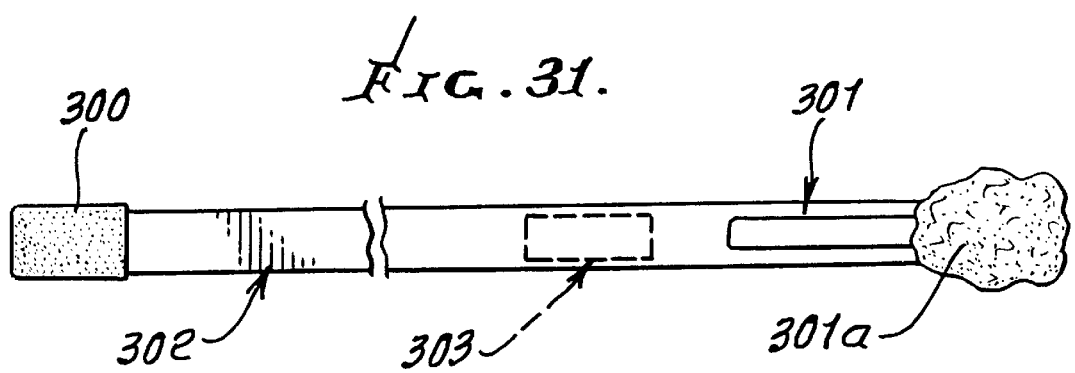

FIGS. 28 and 29 are side and top views of carrier and treatment apparatus, in generally useful form; and FIGS. 30 and 31 are like FIGS. 28 and 29 and show modified carrier and treatment apparatus.

DETAILED DESCRIPTION

FIGS. 28 and 29 show a preferred apparatus for detecting first and second conditions in the vagina or urethra. Such apparatus includes elements in combination, comprising:

a) an elongated carrier insertible endwise into the vagina, b) first structure at a first location on the carrier for use in detecting said first condition, c) and second structure at a second location on the carrier for use in detecting said second condition, d) portions of the first and second structures being inserted into the vagina or urethra, by manipulation of the carrier, and to be subsequently withdrawn, for use in detecting said conditions.

The first structure 300 may be a pH detection means, as described below, and the second structure 301 may be a pathogenic bacterial detection means. Incorporation of both and at opposite ends of a common carrier 302, such as a stick, facilitates rapid testing of two conditions, by the user, at essentially one time, as well as ease of testing. The second structure 301 may include a reactant container on the carrier, and positioned for allowing contact of reactant with vaginal or urethral moisture on that portion of the second means insertible into the vagina or urethra; and the portion of the second means insertible into the vagina or urethra includes a swab 301a for collecting vaginal moisture.

FIGS. 30 and 31 are the same as FIGS. 28 and 29, but incorporate a third structure 303 on the carrier between 300 and 301, to provide release of a secondary odor corresponding to a primary odor created during use of the second structure, for odor comparison purposes. The third structure may include a cover 303a releasably adherent to the carrier, and a secondary odor source substance 303b in a pocket 303c on the carrier concealed by said cover. After removal of the cover, the user can rapidly compare the odors from source 303b and from the second structure 301 to determine presence of pathogenic bacteria.

More particularly, and in FIG. 1, an elongated assembly 10 is shown to include an elongated carrier 11 such as a stick, (corresponding to 302) and a swab 12 (corresponding to swab 301a) as for example a sponge, or other porous material, at the forward end of the assembly. The swab is used to absorb moisture from the vaginal cavity 13, during use of the assembly. FIG. 1 shows a user's finger and thumb 20 and 21 manipulating the assembly.

Controllable test liquid supply means is provided at 14, between the forward end of the carrier 11 and the swab 12. The means 14 is adapted to be manually squeezed to effect controllable communication of contained test liquid to the swab 12, for reaction with vaginal moisture picked up by the swab. Since the supply means or unit 14 is located between 11 and 12, it provides a test means incorporated in or on the assembly 10.

FIG. 2 shows the means or unit (corresponding to 301) as incorporating an outer container 16 which is elongated and tubular, having cylindrical side wall 17, and end wall 18 attached to the forward end of carrier 11. The interior 19 of the container communicates with swab 12, and for this purpose the swab may be received into the open forward end portion 17a of the outer container, thereby mounting the swab to the container.

Figure 3:
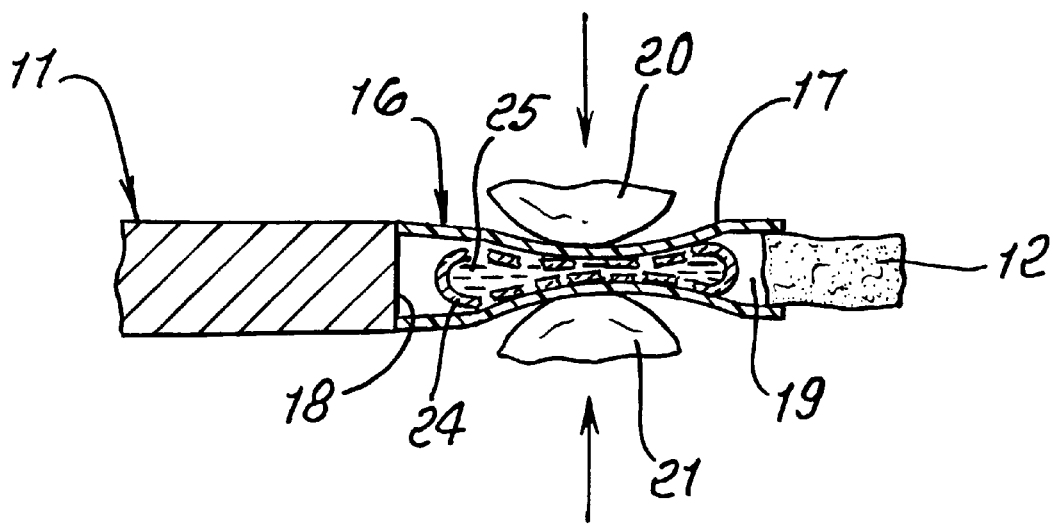
FIG. 3 is a view like FIG. 2, showing manual fracture or rupture of an inner container located within an outer container, as also seen in FIG. 2.
Figure 4:
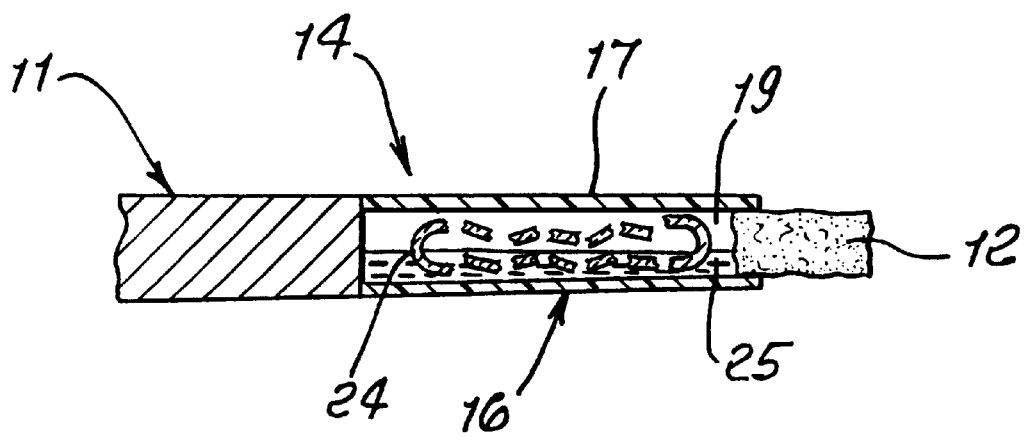
FIG. 4 is a view like FIG. 3, showing liquid from the inner container having been released into the interior of the outer container.
Figure 5:
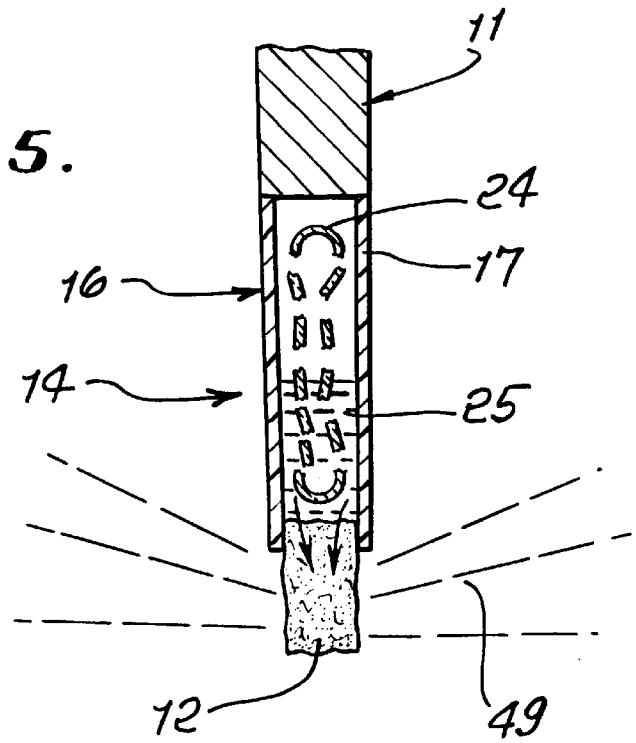
FIG. 5 is a view like FIG. 4, the liquid having flowed from the interior of the outer container to a swab at the end of the assembly, for mixing with vaginal moisture in the swab.

A frangible inner container 24 is located within the interior 19 of container 16, and may be elongated, as shown. Container 24 may consist of a hollow, thin-walled glass capsule to contain test liquid 25. The outer container side wall 17 may consist of relatively stiff plastic material, which is sufficiently flexible to be bent or squeezed, as by or between user's finger and thumb 20 and 21, as seen in FIG. 3. Such bending or squeezing, exerting pressure on the outer container, is sufficient to rupture the inner container as seen in FIG. 3, thereby releasing contained reactant test liquid 25 into the interior 19 of the outer container. See FIG. 4. This provides for controlled access of the test liquid to the swab, for reaction with the vaginal moisture, as seen in FIG. 5. See orientation of the assembly 10 to cause gravitation of the test liquid to flow into contact with the end of the swab carried by the forward end portion of the outer container.

In one form of the invention, the test liquid consists of dilute aqueous alkaline liquid for reaction, as with bacteria in the vaginal moisture in the swab. Such bacteria may be pathogenic. One example of the alkaline test liquid is a 10% to 20% aqueous solution of potassium hydroxide. When such solution contacts amines resulting from bacterial activity, a characteristic odor is produced, as by formation of gaseous amines such as cadaverine and/or putrescine indicated at 49. The user may thereby quickly and efficiently determine the existence of bacteria such as pathogenic bacteria in the vaginal moisture, using a simple unitary test means and procedure as described.

Figure 6:
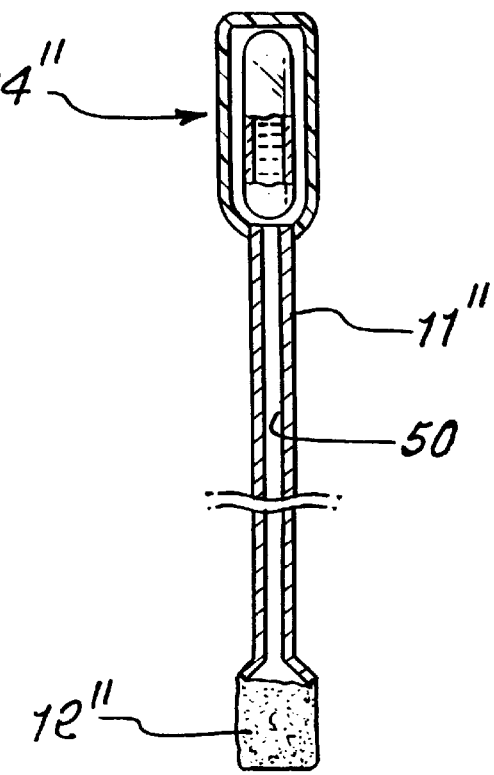
FIG. 6 is a view like FIG. 2, showing a modification.

FIG. 6 shows a modification in which the test liquid supply means 14" is like 14, but located and supported at the opposite end of the carrier 11". A duct 50 is provided in the carrier to communicate the released liquid to the swab 12". The user can manipulate the stick and swab, and also control test liquid delivery to the swab, from the remote or external end of the carrier. Note the reduced diameter of the carrier.

Figure 7:
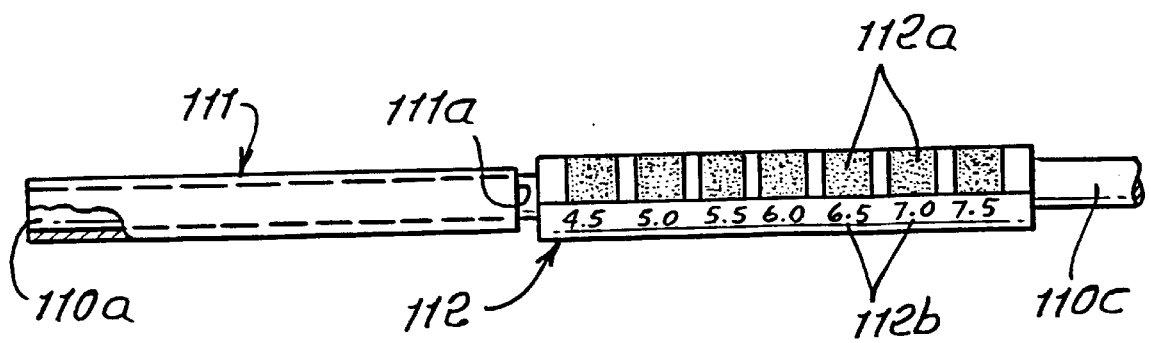
FIG. 7 is an enlarged view of a pH detection means on a carrier, such as is also shown in FIG. 1.

FIG. 7 shows provision of a pH detection means as described in U.S. Pat. Nos. 5,577,512; 5,425,377; and 5,735,801 incorporated herein by reference. Such detection means corresponds to that indicated at 300 in FIG. 28.

As shown in FIG. 7, a first means 111 may comprise a pH indication strip, such as a Nitrazine® Phenaphthazine strip, wound about the stick or carrier end portion 110a and adhered to same as by an adhesive. A color comparison pH measurement means 112 may comprise a thin paper strip adhered to the stick surface to extend lengthwise of the stick from the edge or end 111a of the first means 11. The stick shown corresponds to stick 302 of FIG. 28. A second means is shown to have color gradations in a series sequence, as in colored bands 112a positioned lengthwise of or along the stick. In addition, the paper strip 112 may include pH numerical indicators 112b along side the color gradation bands, to enable:

visual color comparison of the pH indication means 111 (immediately after its exposure to vaginal fluid) with the bands 112a, for visual selection of that band most close in color to the color of the indication means 111;

and immediate visual readout of the pH number adjacent the selected band.

The stick projects freely at 110c away from the first and second means 111 and 112 for manual manipulation to first obtain pH indication of vaginal moisture at one end of the stick, and to enable visual interpretation of that indication by color comparison with the second means, without manual release of the stick. The stick or carrier is then used to obtain a test for bacteria presence in vaginal fluid, as described above. The stick is then disposable, or may be disposed of, after a swabbing step to be described.

Figure 8:
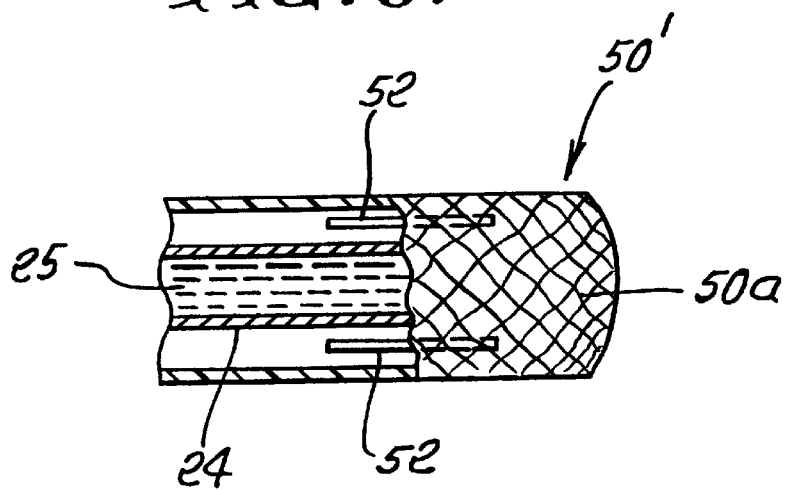
FIG. 8 is a side view showing a modification.

FIG. 8 shows another form of the invention, elements of which correspond to elements of FIGS. 1–7 bearing the same identifying numerals.

In FIG. 8, the outer container has porous means associated therewith, to communicate with the interior of the outer container. The provision of such porous means enables reactant flow of reactant fluid directly released from the fractured inner container into the porous means for reaction with vaginal moisture absorbed into the porous means. Accordingly, flow of reactant fluid to a separate area spaced endwise from the container is not required.

As shown, part or all of the outer container 50' defines an associated porous means, as in the form of a wall 50a consisting of flexible woven material located for example at the end of the assembly. The woven material may consist of synthetic or nonsynthetic material, closely woven in a warp and woof pattern, and may include stiffener means associated therewith to assist in maintaining the tubular shape of the outer container. See for example stiffener elements 52.

When squeezed, the outer container deflects to transmit force to the inner container 24 to fracture its wall. This effects release of the reactant fluid into the interior 19 of the outer container and direct access of said reactant fluid to vaginal moisture absorbed into interstices formed by porous means which may be defined by the outer container or part thereof. Such squeezing of the outer container also tends to displace moisture therein toward the reactant fluid, for reaction therewith as described above. A more direct testing method is thereby provided.

The fluid capsule 24 may contain a dye of such color as to make it clear that the fluid in capsule 24 has permeated the sponge 12 or woven cover 50a, during use. Usable dyes include Methylene Blue USP 1% (10 mg/ml)

NDC 0517-0373-70

Indigo Carmine 0.8% solution

NDC 0517-0375-10

Both dyes are approved for IM or IV use by the U.S. Food and Drug Administration.

The test liquid released from the inner container may be used to react with vaginal moisture absorbed by or on the porous means 12, for detection of estrogen level. See in this regard my pending application Ser. No. 08/570,534, filed Dec. 11, 1995, and U.S. Pat. No. 5,735,801, incorporated herein by reference.

As referred to, use of the means 300 at the opposite end of the stick concerns determining need for estrogen replacement therapy, or estrogen or estradiol dose change, through vaginal wall moisture pH determination or urethral wall moisture pH determination. Typical steps of such usage include:

a) determining local acidity proximate a moist wall surface of the vagina or urethra, as differing from desired threshold level, as in the substantial absence of bacterial vaginosis, or other contaminants such as medication, blood, semen, b) and administering sufficient estrogen or estradiol to result in change in said acidity toward said level.

A more complete method includes:

a) first determining local acidity proximate a moist wall surface of the vagina, said determining employed as an indicator of the presence or absence of bacterial vaginosis, b) and, after a vaginosis condition has been treated and eliminated, then again determining local acidity proximate a moist wall surface of the vagina, as differing from desired threshold level, c) and administering sufficient estrogen or estradiol to result in change in said acidity toward said threshold level.

A pH indicator 100, as seen in FIG. 21 may be employed, and that indicator may be located at one end of a carrier 101, like carrier 302 which is easily manipulable into contact with the vaginal or urethral wall, shown at 102, (after or before use of device 301) the user's finger shown at 103 to urge the tissue strip toward the wall surface. Such an indicator may take the form of one of the following, although other indicators are usable.

i) NITRAZINE® paper
ii) phenaphthazine on a carrier
iii) a material or materials exhibiting different colorations or other indicators as a function of pH level.

The indicator may desirably exhibit different colorations or changes corresponding to different pH levels, of moisture at the vaginal or urethral wall, and from which the observed coloration or changes may be used to indicate need for greater or lesser estrogen or estradiol dosage, as on a daily or other periodic basis. In the case of NITRAZINE® paper (phenaphtazine), the correlation of pH to color is as follows:

| pH | Color |
|---|---|
| 4.5 | golden yellow |
| 5.0 | beige |
| 5.5 | light olive |
| 6.0 | dark olive |
| 6.5 | olive blue |
| 7.0 | purple blue |
| 7.5 | dark blue |

In a typical example, if the user detected or determined an indicator color of dark olive, it would be determined that an estrogen or estradiol increase above the existing daily level of use would be recommended, in order to diminish pH level to 4.2 to 4.5 within one to two weeks, for example. Testing would be performed on a once a week basis. Thus, if the user had been taking 1 mg. of estrogen or estradiol per day, for example orally, she would be recommended to increase that level to 1.5 mg. per day, the objective being to reduce the pH level to about 4.5 within about 10–21 days. If the tested color were not golden yellow (4.5 pH) after 7–8 days, the dosage might be increased to 2.0 mg. level, per day, until a goldenrod yellow color of the test strip was achieved. Thus, pH determination is indicative of need for change in estrogen or estradiol dosage (up or down).

In FIGS. 9–12, an elongated, narrow carrier stick 10' may consist of wood, plastic, or other material. Provided on the carrier stick are:

a pH indication means, as generally shown at 11', at one end portion 10a' of the stick; and a color comparison pH measurement means, as generally indicated at 12', spaced from stick end portion 10a', but close to 11';

As shown, the first means 11' may comprise a pH indication strip, such as a NITRAZINE® (Phenaphthazine) strip, wound about the stick end portion 10a' and adhered to same as by an adhesive. NITRAZINE® (Phenaphthazine) strips are products of Bristol-Myers Squibb. The color comparison pH measurement means 12' may comprise a thin paper strip adhered to the stick surface to extend lengthwise of the stick from the edge or end 11a' of the first means 11'. The second means is shown to have color gradations in a series sequence, as in colored bands 12a', positioned lengthwise of or along the stick. In addition, the paper strip 12' may include pH numerical indicators 12b' along side the color gradation bands, to enable:

visual color comparison of the pH indication means 11' (immediately after its exposure to vaginal or urethral fluid or moisture) with the bands 12a', for visual selection of that band most close in color to the color of the indication means 11';

and immediate visual readout of the pH number adjacent the selected band.

Such readout of pH is then compared with the desired level of about 4.2–4.5 to enable determination of a recommended dosage of estrogen or estradiol, as on a daily basis.

The stick projects freely at 10c, away from the first and second means 11' and 12' for manual manipulation (see the grasping finger and thumb 18' and 19'), to first obtain pH indication of vaginal or urethral wall moisture at one end of the stick, and to enable visual interpretation of that indication by color comparison with the second means, without manual release of the stick. The stick is then disposable, or may be disposed of.

Lengthwise spacing "d" between 12' and stick end 10d' is such as to enable free manual manipulation of the stick; and such spacing is typically between 3 and 5 inches, enabling ready finger grasping of the stick and manipulation thereof. In a specific example, "d" is about 4 inches, and the stick diameter or width is about 3/16 to 3/8 inch. See also FIGS. 10–12.

The method of measuring pH of vaginal moisture includes the steps:

a) providing a pH indicator on a carrier stick, b) manipulating the stick to obtain pH indication of vaginal or urethral wall moisture at said indicator, c) visually interpreting that indication to determine need for a change in estrogen or estradiol dosage, d) and disposing of the stick, The overall sizes of 11', 12' and 13' are such as to enable ready insertion into the vagina, or urethra, or application to a surface of the vagina or urethra 22, via stick manipulation at zone 10c'.

Referring now to the modification shown in FIGS. 13–15, a smooth surfaced protective tip 20' is provided to face endwise at the end 10aa' of the stick end portion 10a'. As shown, the tip 20' is endwise convex, as for example bulbous, to provide for or enable comfortable insertion of the stick end portion 10a' into the vagina or urethra, for pH measurement. The tip 20' may typically be formed integrally with a sleeve 20a' assembled over and closely fitting the measurement strip 11', and may be suitably adhered thereto, locally, as at 21'. A suitable bonding agent is epoxy. The remainder of the strip 11' is therefore available for pH indication. Alternatively, the sleeve may be attached, as by heat shrinking, or by wedge fit.

A fluid access opening is provided through the wall of the sleeve, whereby vaginal moisture or fluid may access the strip 11' via that opening. See for example elongated slot 22' in the sleeve wall 20aa'. The sleeve and tip may consist of transparent, molded, plastic material, to facilitate viewing of a change of color of the strip 11.

In FIG. 16, the sleeve 20a' is shortened and attached at sleeve end 20a" into flush, or near flush, relation with the surface of the strip, at a locus on stick end portion 10a'. This leaves the remaining length 11f' of the strip openly exposed for moisture contact.

In FIG. 17, the sleeve 20a'" is also shortened and attached to the stick end portion 10a', and in endwise alignment with the strip 11'. This also leaves the remaining length 11f' of the strip openly exposed for moisture contact.

Referring now to the modification seen in FIG. 18, the elements the same as in FIG. 10 are given the same numerals. In addition a protective layer 40' in the form of a thin porous barrier, is applied adjacent the outer side of strip 11' so as to cover the latter (i.e. extend thereabout) and to be carried by the stick. Layer 40' allows vaginal moisture to penetrate through it and to contact the pH indicator strip 11', as during a test. Following the test, the strip 11' may be observed as described above, and for this purpose the layer 40' may be at least partly removed from adjacency to the strip, as by complete manual removal. Opposite end portions 40a' and 40b' of layer 40' may be initially attached as by light bonding or sticking to the ends of the strip 11', or to the stick, allowing pull-away removal of the layer at the end of the test. Such bonding agents are known, as on 3M Micropore Tape. Layer 40' acts as a barrier, during a test, to block direct contact of vaginal tissue or urethral tissue with strip 11', preventing any possible irritation of such tissue.

In FIG. 19, the elongated layer 45' is like layer 40', but also extends over and about the color comparison measurement means 12', and is adhered, as described above, to the elements 11' and 12', as at 45a' and 45b' to completely cover 11' and 12' as during a test, while allowing pull-away of the layer 45' for visual observation of 11 and 12 after the test. Either one or both of 11' and 12' may be considered as a pH detecting means.

FIG. 20 is like FIG. 16, but layer 50' corresponding to layer 40' has its end 50a' adhered to and about the sleeve 20a", while end portion 50b' is adhered to the right end of strip 11', as shown. Note smooth surfaced blunt knob 20', as referred to above.

FIG. 20a is like FIG. 20, except that the layer 60', corresponding to 50', is elongated to cover the color comparison measurement means 12', and to adhere at 60b' to the rightward end of 12'.

In FIGS. 18–20a, the porous barriers, as at 40', 45', 50' and 60' may consist of one or more barrier tissue layers, as for example are used in incontinence pads. One example is the outer layer of the Kimberly Clark product NEW DEPEND. Another usable barrier is the 3M product known as MICROPORE tape. One side of such tape is "tacky", i.e. weakly adhesive, so that it will adhere along the tape length to the elements 11' and/or 12' referred to. Barriers 45' and 50' as referred to may comprise such tape material.

In FIGS. 22–25, a modified elongated, narrow carrier stick 200 may consist of wood, plastic or other carrier material. A pH indication strip 201 such as phenaphthazine paper is adhered to one substantially flat side 200a of the stick 200, and near one end 200b, as by an adhesive. The strip 201 is elongated, and spaced from opposite edges 200c and 200d of the stick, as well as from end 200b. Typically, rectangular strip width is about 0.25 inches, and its length is about 1.5 inches. The stick width is about 0.375 inches, its length is about 5 inches and its thickness is about 0.125 inches.

The stick edges 200c and 200d are convexly curved or rounded as at 210 and 211 in FIG. 25. Also, the stick opposite ends 200f and 200g are convexly curved or rounded as at 212 and 213.

The handle portion 200e of the stick is desirably textured, as by provision of dimples 215 on side 200a of the stick. The length of such texturing may be about 1.5 inches, from end 200b. Such texturing aids finger and thumb gripping of the handle portion for accurate stick manipulation to position strip 201 adjacent the vaginal wall. Aiding of manipulation of the paper strip is enhanced by locating the texturing and paper strip at the same side of the stick. Note that the stick preferably has smooth top surface extent at 220 between 215 and 201, and also a smooth bottom surface at 221. Stick 200 may be extended to support or carry bacteria test structure as at 201 described above. See FIG. 24. Such a stick may be received in a receptacle indicated at 230', and like receptacle 230 described above.

FIGS. 26 and 27 show yet another and preferred kit in which an indicator strip or tip 228 (corresponding to strip or tip 111) is carried at the left end of elongated stick 229. A swab 233 is carried at the right end of the stick. An encapsulating, thin, flexible, transparent receptacle 230 protectively contains the elongated stick, tip 228 and swab 233, and may be torn open to retrieve the stick. The receptacle may consist of thin walled plastic sheets 230a and 230b bonded together along sheet edge portions indicated at 250, 251, 252 and 253, whereby the receptacle is sealed.

A thin, elongated paper insert sheet 260 is also received in the receptacle, to overlie most of stick 200, whereby use instruction and identification data may be printed on the sheet 260 and presented upwardly or outwardly for viewing through the transparent upper sheet 230a. Sheet 260 defines a narrow window or cut-out at 261, which is elongated along a mid-portion 262 of sheet 260, as shown.

Color comparison elements such as bands are carried by the insert sheet 260, as in two rows shown at 228a and 228b, at opposite sides of the window. Preferably, the longitudinally spaced bands extend to laterally spaced edges of the window, for ease of color comparison of the indicator (after its exposure to moisture as described above) with the different bands. Sheet 260 may be eliminated, and the bands printed or affixed on the receptacle top sheet, to define the window.

Longitudinally spaced bands have different colors, while laterally oppositely spaced bands have the same color. Note their pH numerical labeling, at 4.5, 5.0, 5.5, 6.0, 6.5, 7.0, and 7.5, along the window length.

In use, the right end of the receptacle is opened, and the carrier stick 229 is withdrawn, for use. Thereafter, the indicator tip 228, which may be cylindrical, after its exposure to moisture, is re-inserted into the elongated receptacle 230, under the insert sheet 260, to bring tip 228 under the window 261. Tip 228 preferably has a width or diameter greater than the window width, so that it adjacently registers with the successive bands in the two rows as the tip moves longitudinally. This facilitates ease of color comparison use. The tip and stick remain in the receptacle, for ease of disposal.

In addition to provision and manipulation of a first carrier stick as referred to, with respect to vaginal or urethral moisture samples, the method may also include providing an elongated second carrier having a second pH detector on that carrier at an end position thereof, and manipulating the second carrier to effect exposure of the second detector to vaginal or urethral moisture, thereby to cause the second detector to exhibit a color change, and comparing the color changes exhibited by the first and second detectors. If color changes exhibited (due to both vaginal and urethral moisture contact with the detector) are the same, a validity check is thereby provided.

Accordingly, the method of determining validity of pH of body moisture or fluid may include:

a) determining pH of vaginal moisture or fluid, by employment of a first indicator, b) also determining pH of urethral moisture or fluid, by employment of a second indicator. The two indicators may then be compared, as for example by comparison of color changes produced on or by the indicators. The indicators themselves would be identical as to color change capability.

If a stick as in FIG. 24 is used, or a similar stick, its opposite end can easily be used to determine presence of pathologic bacteria.

EXAMPLES

Objectives

To confirm the elevation of vaginal pH expected in patients with bacterial vaginosis and to examine the relationship of serum FSH and estradiol levels to vaginal pH in normal patients without vaginosis.

Study Design 2,038 patients in a solo private practice underwent measurement of vaginal pH during routine pelvic examinations. 201 of these patients were chosen at random for this study. Measurements were made of serum levels of FSH and estradiol. Vaginal cultures were taken from 83 patients. Specimens were sent to a single commercial laboratory. Vaginal pH was determined by phenaphthazine (NITRAZINE®) pH paper. Vaginal pH was correlated with serum FSH, estradiol levels, and vaginal cultures using statistical analysis.

Results

Vaginal pH was elevated in patients with documented vaginosis. Serum estradiol levels showed an inverse and serum FSH levels showed a direct statistical correlation with vaginal pH.

Materials and Methods

Between May 1995 and May 1996, 2,038 patients in a private gynecologic practice were tested for vaginal pH. None of the patients were pregnant.

A total of 83 patients had vaginal cultures to study the effect of vaginosis on vaginal pH.

Two hundred one patients were tested for vaginal pH, serum FSH and serum estradiol. Of these 201 patients, 100 were on Estrogen Replacement Therapy and 8 were on oral contraceptives. Ninety-three patients were on no hormonal treatment. No patients tested were using vaginal medication.

Eighteen patients were tested for vaginal pH, serum FSH and serum estradiol on two separate occasions. Nine of these patients were tested before and after the use of estrogen. Nine patients were tested after a change in estrogen dose. In all nine cases, the estrogen does was increased. This separate study was done to observe the change in vaginal pH, serum FSH and serum estradiol in response to a change in estrogen therapy.

Phenaphthazine (NITRAZINE®) pH indicator paper was used for vaginal pH testing (NITRAZINE® pH indicator paper pH 4.5 to 7.5 range, distributed by APOTHECON®, a Bristol-Myers Squibb Company, Princeton, N.J.). This pH paper has been used for vaginal pH testing since 1938. The extended range of pH 4.5 to 7.5 proved to be easier to read and more comprehensive for vaginosis and vaginal estrogen level. Other pH testing papers were tried. (Hydrion® pH papers, Micro Essential Laboratory, 4224 Avenue H, Brooklyn, N.Y. 11210 (718) 338-3618). (ColorpHast® pH test strips, EM Science, 480 Democrat Road, Gibbstown, N.J. 08027 (800) 222-0342).

The pH paper was applied directly to the lateral vaginal wall at the outer third of the vagina. Care was taken to avoid cervical mucous (pH 7.0), blood (ph 7.4), or other substances (such as semen pH 7.0–8.0) and lubricating jelly known to affect vaginal pH. All samples were interpreted in incandescent light for accuracy.

All vaginal cultures were collected using the Star Swab, Starplex Transport System and were sent to Unilab Corporation, Tarzana, Calif. Venopuncture for blood samples was obtained within one hour of the vaginal pH test. Serum FSH was run on the Dade/Baxter, Inc. Stratus II automated instrument and reported as miU/mL. Female normal ranges are: Follicular Phase: 3.6–16.0 miU/ml, Mid Cycle Peak: 8.1–28.9 miU/ml, Luteal Phase: 1.8–11.7 miU/mL and Post Menopausal: 22.9–167.0 miU/mL. Serum estradiol was determined by radio immune assay, using Diagnostics Products Corporation's Coat A Count and reported as pg/mL. The normal range is 10–375. All tests were done at Huntington Memorial Hospital laboratory, Pasadena, Calif. Statistical analysis was performed by using the computer program "Statistical Package for Social Sciences" (SPSS).

Relationships between vaginal pH, serum estradiol and FSH levels were evaluated using Spearmans's Correlation Coefficients. Treated and untreated groups were compared for these variables using t-tests and ANOVA with Duncan Multiple Comparisons. Paired t-tests were used to compare the difference in means due to initiation or change of estrogen therapy.

Results

Of 84 patients who had vaginal cultures, 27 grew normal flora, 14 yeast, 15 Beta-hemolytic-streptococcus, 14 gardnerella, and 13 mixed pathogens. The mean pH of three subgroups with bacterial vaginosis is significantly higher than that obtained in patients with either normal flora or yeast infection (One way ANOVA, $p<0.05$). There was no significant difference in the vaginal pH among the three subgroups with bacterial vaginosis, and there was no significant difference between the pH in patients with yeast infection and those with normal flora.

In the overall group of 201 women tested for vaginal pH, estradiol and FSH, vaginal pH correlated positively with serum FSH levels and negatively with serum estradiol using Spearman's correlation coefficients.

When the group of 201 women was divided into those on estradiol therapy and those on no treatment, significant differences were found between mean vaginal pH, serum estradiol levels, and serum FSH levels. These differences were significant despite the inclusion of some apparently normally cycling women in the untreated group. There was no significant difference in the mean age of the patients between the two groups.

The characteristics of 18 women studied both before and after initiation (n=9) or change (n=9) of estrogen replacement therapy showed that serum estradiol levels increased and FSH levels decreased significantly after initiation or changes of dose of ERT ($p<0.003$ and $p<0.001$ respectively, using paired t-testing). There was a significant decrease in vaginal pH from 6.1±0.7 to 4.6±0.3 ($p<0.001$) in the group who went from no treatment to estrogen replacement. Mean vaginal pH also decreased, although to a lesser degree of significance, in the women who went from lower dose to higher dose ERT (p=0.05).

The data obtained support the well documented body of literature indicating that vaginosis results in an elevated vaginal pH (5.0–6.5). For this reason alone, vaginal pH should become a routine test during most speculum examinations. Women should be encouraged to do vaginal pH testing to alert both pregnant and non-pregnant women to the possibility of sub-clinical vaginosis and to seek medical advice for proper diagnosis and treatment. The combination of pH testing, vaginal culture, and treatment as indicated, have shown a decrease in premature rupture of membranes and premature delivery.

The editorial comments of Watson A. Bowes, Jr. in the May 1996 issue of Obstetrical and Gynecological Survey are pertinent.

Statistically significant is the fact that the vaginal pH level, in the absence of vaginosis, is a reasonable marker for most patient's estradiol status. In addition, an elevated vaginal pH level in a well estrogenized patient is a reasonable marker for vaginosis. In this regard, detected pH correlates positively (directly) with FSH; and pH correlates negatively (inversely) with estradiol intake.

In consideration of all that as been said, vaginal and/or urethral testing for pH level appears to be that hoped for, reliable, "low-tech" tool. It certainly complies with the mandate for cost-effective, improved health care.

In the above, estrogen or estradiol can be administered orally, intermuscularly, or vaginally.

I claim:

1. In apparatus for detecting first and second conditions in the vagina or urethra, the combination comprising
    a) an elongated carrier insertible endwise into the vagina,
    b) first structure at a first location on the carrier for use in detecting said first condition,
    c) and second structure at a second location on the carrier for use in detecting said second condition,
    d) portions of the first and second structures being inserted into the vagina or urethra, by manipulation of the carrier, and to be subsequently withdrawn, for use in detecting said conditions,
    e) said second structure comprising a pathogenic bacteria detection means including a flowable fluid reactant container configured to allow controlled release of reactant fluid to react with bacteria containing vaginal or urethral moisture.

2. The apparatus of claim 1 wherein said first structure is a pH detection means.

3. The apparatus of claim 1 wherein said second structure includes a surface or surfaces positioned for allowing contact of reactant with vaginal or urethral moisture on said surface or surfaces insertible into the vagina or urethra.

4. The apparatus of claim 3 wherein said surface or surfaces are defined by a swab for collecting vaginal moisture.

5. The apparatus of claim 1 wherein said first structure is a pH detection means for detection of vaginal moisture pH.

6. The apparatus of claim 5 wherein said pH detection means is located on the carrier, relatively remotely from said second structure.

7. The apparatus of claim 6 wherein said first and second structures are located at opposite ends of the carrier.

8. The apparatus of claim 6 including:
    a) a support package,
    b) color comparison measurement elements carried by the package to allow their comparison with said pH detector after exposure of said detector to moisture the pH of which is to be determined.

9. The apparatus of claim 8 wherein the package includes a base and a receptacle on the base, the carrier and pH detector means removably received in the receptacle.

10. The apparatus of claim 9 wherein the color comparison measurement elements are on one of the following:
    i) the support base
    ii) the receptacle.

11. The apparatus of claim 9 wherein the receptacle is sufficiently transparent to allow viewing of the detector in the receptacle for color comparison with said elements outside the receptacle.

12. The apparatus of claim 8 including additional means on the carrier to provide release of a secondary odor corresponding to a primary odor created during said use of said second structure.

13. The apparatus of claim 12 wherein said additional means comprises a cover releasably adherent to the carrier, and a secondary odor source on the carrier concealed by said cover.

14. In apparatus for detecting first and second condition in the vagina or urethra, the combination comprising
    a) an elongated carrier insertible endwise into the vagina,
    b) first structure at a first location on the carrier for use in detecting said first condition,
    c) and second structure at a second location on the carrier for use in detecting said second condition,
    d) portions of the first and second structures being inserted into the vagina or urethra, by manipulation of the carrier, and to be subsequently withdrawn, for use in detecting said conditions,
    e) said second structure comprising a pathogenic bacteria detection means, which includes:
        i) a flexible outer container supported on the carrier,
        ii) a vaginal moisture absorbing swab at one end of the carrier to communicate with the interior of said outer container,
        iii) a frangible inner container protectively located within the outer container, and a flowable aqueous alkaline fluid reactant within the inner container,
        iv) whereby pressure exerted on the outer container sufficient to rupture the inner container thereby releases said reactant into the interior of the outer container to enable reactant fluid flow to said swab, for reaction with bacteria containing vaginal moisture absorbed into the swab,
        v) and whereby a gaseous product of said reaction maybe detected, by characteristic odor.

15. The apparatus of claim 14 wherein said aqueous alkaline fluid reactant consists essentially of a dilute aqueous solution of potassium hydroxide.

16. The apparatus of claim 15 wherein said solution consists of 10 to 20% potassium hydroxide.

17. The apparatus of claim 14 wherein said outer container is located in relatively close association with said swab.

18. The apparatus of claim 14 wherein said outer container is located at a position on the carrier that is relatively remote from the swab.

19. The apparatus of claim 18 including a duct associated with the carrier to convey fluid reactant from the container interior to the swab.

20. The apparatus of claim 14 wherein said carrier is elongated for manipulation to cause the outer container to exert endwise and sidewise force on the swab to cause the swab to absorb vaginal moisture, in the vagina.

21. The apparatus of claim 14 including a third structure on the carrier to provide release of a secondary odor corresponding to a primary odor created during said use of said second structure.

22. In apparatus for detecting first and second conditions in the vagina or urethra, the combination comprising
 a) an elongated carrier insertible endwise into the vagina,
 b) first structure at a first location on the carrier for use in detecting said first condition,
 c) and second structure at a second location on the carrier for use in detecting said second condition,
 d) portions of the first and second structures being inserted into the vagina or urethra, by manipulation of the carrier, and to be subsequently withdrawn, for use in detecting said conditions,
 e) and including a third structure on the carrier to provide release of a secondary odor corresponding to a primary odor created during said use of said second structure.

23. The apparatus of claim 22 wherein said third structure comprises a cover releasably adherent to the carrier, and a secondary odor source on the carrier concealed by said cover.

24. In the method of detecting first and second conditions in the vagina, the steps that include:
 a) providing an elongated carrier insertible endwise into the vagina,
 b) providing first structure at a first location on the carrier for use in detecting said first condition,
 c) providing second structure at a second location on the carrier for use in detecting said second condition, said second structure comprising a pathogenic bacteria detection means including a flowable fluid reactant container configured to allow controlled release of reactant fluid to react with bacteria containing vaginal or urethral moisture,
 d) and inserting portions of said first and second structure into the vagina, by manipulation of the carrier, to be subsequently withdrawn, for use in detecting said conditions.

25. The method of claim 24 wherein said first structure is provided in the form of a pH detection means.

26. The method of claim 24 wherein said second structure is provided to include a surface or surfaces positioned for allowing contact of reactant with vaginal moisture on said surface or surfaces insertible into the vagina.

27. The method of claim 26 wherein said surface or surfaces are defined by a swab for collecting vaginal moisture.

28. In the method of detecting first and second conditions in the vagina, the steps that include:
 a) providing an elongated carrier insertible endwise into the vagina,
 b) providing first structure at a first location on the carrier for use in detecting said first condition,
 c) providing second structure at a second location on the carrier for use in detecting said second condition,
 d) and inserting portions of said first and second structures into the vagina, by manipulation of the carrier, to be subsequently withdrawn, for use in detecting said conditions,
 e) said second structure being provided in the form of a pathogenic bacteria detection means,
 f) said method further including
  i) providing said pathogenic bacterial detection means to include a flexible outer container supported on the carrier, the interior of the outer container configured to communicate with a porous portion of the second structure insertible into the vagina,
  ii) providing a frangible inner container protectively located within the outer container, and providing a flowable aqueous alkaline fluid reactant within the inner container,
  iii) exerting pressure on the outer container sufficient to rupture the inner container, thereby releasing said reactant interior of the outer container to enable reactant fluid into the flow to said porous portion having bacteria containing vaginal moisture absorbed into the porous portion,
  iv) whereby a gaseous product of said reaction may be detected, by characteristic odor.

29. The method of claim 28 wherein said porous portion is defined by the outer container.

30. The method of claim 28 wherein said porous portion is defined by woven material.

31. The method of claim 28 wherein said aqueous alkaline fluid reactant consists essentially of a dilute aqueous solution of potassium hydroxide.

32. The method of claim 31 wherein said solution consists of 10 to 20% potassium hydroxide.

33. The method of claim 28 including manipulating said carrier to cause the outer container to exert endwise and sidewise force on said porous portion causing the porous portion to absorb vaginal moisture, in the vagina.

34. The method of claim 28 also including providing said first structure in the form of a pH detector for detection of vaginal moisture pH, in conjunction with performing the steps of claim 28.

35. The method of claim 34 including manipulating said carrier to effect exposure of said detector to vaginal moisture, thereby to cause said detector to exhibit a color change.

36. The method of claim 35 including providing a pH correlating color comparison measurement means, in sufficiently close association with said carrier and with said detector to allow visual comparison of the changed color exhibited by said detector with a pH correlated color provided by said measurement means.

37. The method of claim 36 including providing a package for supporting said carrier and said color comparison measurement means.

38. The method of claim 37 including providing for removable containment of said carrier by said package.

39. The method of claim 36 wherein said detector is provided in the form of an elongated strip and said color comparison measurement means is provided in the form of a strip of material that is elongated in a direction related to the elongated direction of said detector strip to facilitate said color comparison.

40. The method of claim 36 that includes relatively moving said color comparison measurement means and said carrier to achieve said close association of said color comparison measurement means with said detector.

41. The method of claim 39 that includes relatively moving said color comparison measurement strip of material and said carrier, to effect relative movement of said color comparison measurement means in close association with said detector strip.

42. The method of claim 39 including providing a package for said carrier, and locating said color comparison measurement strip on said package.

43. In the method of detecting first and second conditions in the vagina, the steps that include:

a) providing an elongated carrier insertible endwise into the vagina, b) providing first structure at a first location on the carrier for use in detecting said first condition, c) providing second structure at a second location on the carrier for use in detecting said second condition, said second structure comprising a pathogenic bacterial detector, and providing a flowable fluid reactant container configured to allow controlled release of reactant fluid to react with bacteria containing vaginal or urethral moisture on said detector, d) and inserting portions of said first and second structures into the vagina, by manipulation of the carrier, to be subsequently withdrawn, for use in detecting said conditions.

44. The method of claim 43 wherein said first structure is provided in the form of a pH detection means.

* * * * *